United States Patent [19] [11] 4,379,927
Vorbrüggen et al. [45] Apr. 12, 1983

[54] PROCESS FOR THE PREPARATION OF IMIDAZOLEACETIC ACID DERIVATIVES

[75] Inventors: Helmut Vorbrüggen; Norbert Schwarz, both of Berlin, Fed. Rep. of Germany

[73] Assignee: Schering Aktiengesellschaft, Berlin and Bergkamen, Fed. Rep. of Germany

[21] Appl. No.: 349,416

[22] Filed: Feb. 16, 1982

[30] Foreign Application Priority Data

Feb. 13, 1981 [DE] Fed. Rep. of Germany ....... 3106150

[51] Int. Cl.³ .................. C07D 413/06; C07D 233/64
[52] U.S. Cl. .................................... 544/139; 544/238; 544/333; 544/405; 546/121; 546/146; 546/147; 546/167; 546/278; 546/210; 548/204; 548/235; 548/255; 548/262; 548/324; 548/336; 548/342; 260/245.5
[58] Field of Search ............... 548/255, 262, 204, 235, 548/324, 336, 342; 546/146, 147, 167, 121, 278, 210; 544/139, 238, 333, 405; 260/245.5

[56] References Cited
FOREIGN PATENT DOCUMENTS
524617 8/1972 Switzerland .

OTHER PUBLICATIONS
Katriteky et al., *Advances in Heterocyclic Chemistry*, vol. 27, (1980), pp. 251-252.

Primary Examiner—Robert W. Ramsuer
Attorney, Agent, or Firm—Millen & White

[57] ABSTRACT

A process for preparing imidazoleacetic acid derivatives of Formula I

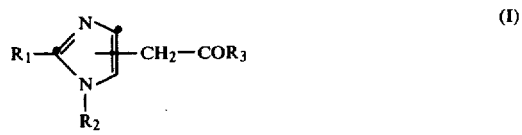

wherein
$R_1$ is hydrogen, alkyl, cycloalkyl, aralkyl, aryl, a heterocyclic group, amino, or amino substituted by alkyl, cycloalkyl, aralkyl, or aryl,
$R_2$ is hydrogen, alkyl, cycloalkyl, aralkyl, aryl, or a heterocyclic group,
$R_1$ and $R_2$ together form a ring, and
$R_3$ is alkoxy, aralkoxy, amino, mono- or dialkylamino, pyrrolidino, piperidino, morpholino, or arylamino or heteroarylamino, each optionally substituted in the aryl portion,
comprises reacting the corresponding amidine or guanidine of Formula II

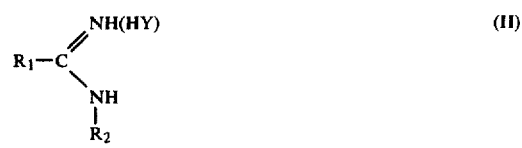

wherein
$R_1$ and $R_2$ are as defined above and
(HY) represents an optional inorganic mineral acid or an organic acid,
with the corresponding acetoacetic acid derivative of Formula III

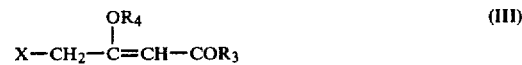

wherein
$R_3$ is as defined above,
X is a halogen, and
$R_4$ is trialkyl- or triaralkylsilyl, alkyl, or aralkyl.

5 Claims, No Drawings

PROCESS FOR THE PREPARATION OF IMIDAZOLEACETIC ACID DERIVATIVES

BACKGROUND OF THE INVENTION

This invention relates to a process for the preparation of imidazoleacetic acid derivatives from 4-haloacetoacetic acid derivatives and amidines.

Heretofore, imidazole-4(5)-acetic acids, their esters or amides could be produced only at great expense via several stage processes. Furthermore, pressure had to be employed even in the first stage in an autoclave. Multistage processes have been described by W. Schunack [Archiv Pharmazie 307: 470 (1974)], F. L. Pyman [J. Chem. Soc. 99: 668 (1911)], and in European patent application 5528.

As disclosed in Swiss Pat. No. 524,617, a method which at first sight seems readily applicable, namely to react the readily accessible 4-haloacetoacetic acid esters or amides with amidines, in all instances leads instead to 6-ring formation (6-halomethylpyrimidine) because the halogen in these α-haloketones is not sufficiently reactive.

SUMMARY OF THE INVENTION

Accordingly, it is an object of the invention to provide a simpler and preferable method for preparing such imidazoleacetic acid derivatives.

Upon further study of the specification and appended claims, further objects and advantages of this invention will become apparent to those skilled in the art.

It has now been found that 4-haloacetoacetic acid esters or amides react quite differently with amidines or guanidines if the acetoacetic acid derivatives are first converted into 4-halo-3-trialkylsilyloxy- or -3-alkoxy-crotonic acid esters or amides. The 4-halogen then reacts surprisingly very readily, and the 4-haloacetoacetic acid derivatives react with amidines and guanidines to form 1,2-substituted imidazole-4(5)-acetic acid esters or amides.

Accordingly, the present invention has achieved the mentioned objects by providing a process for preparing imidazoleacetic acid derivatives of Formula I

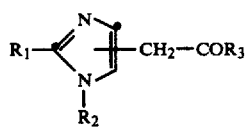

wherein
$R_1$ is hydrogen, straight-chain or branched alkyl, cycloalkyl, aralkyl, aryl, a heterocyclic group, amino, or amino substituted by alkyl, cycloalkyl, aralkyl, or aryl,
$R_2$ is hydrogen, straight-chain or branched alkyl, cycloalkyl, aralkyl, aryl, or a heterocyclic group,
$R_1$ and $R_2$ together form a ring, and
$R_3$ is straight-chain or branched alkoxy, aralkoxy, amino, mono- or dialkylamino, pyrrolidino, piperidino, morpholino, arylamino or heteroarylamino, each optionally substituted in the aryl portion,
comprising reacting the corresponding amidine or guanidine of Formula II

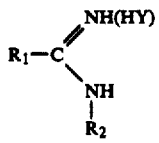

wherein
$R_1$ and $R_2$ are as defined above and
(HY) represents an optional inorganic mineral acid or an organic acid, with the corresponding acetoacetic acid derivative of Formula III

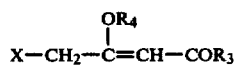

wherein
$R_3$ is as defined above,
X is a halogen, e.g., fluorine, chlorine, bromine, or iodine, and
$R_4$ is trialkyl- or triaralkylsilyl, alkyl, or aralkyl.

DETAILED DISCUSSION $R_1$ and $R_2$ can be the same or different.

Suitable $R_1$ and $R_2$ alkyl groups include straight-chain and branched, saturated hydrocarbon residues of 1-24 carbon atoms, e.g. methyl, ethyl, propyl, isopropyl, butyl, isobutyl, sec-butyl, tert-butyl, pentyl, isopentyl, hexyl, isohexyl, heptyl, octyl, nonyl, decyl, etc., especially those of 1-6 carbon atoms. Suitable $R_1$ and $R_2$ cycloalkyl groups, include those of 5-7 carbon atoms, such as cyclopentyl, cyclohexyl, cycloheptyl, methylcyclohexyl, ethylcyclopentyl, methylcyclopentyl, etc.

Suitable aralkyl groups for $R_1$ and $R_2$ include straight-chain and branched groups of 7-14 carbon atoms, e.g. benzyl, 1-phenylethyl, 2-phenylethyl, 1-phenylpropyl, 2-phenylpropyl, 3-phenylpropyl, 4-phenylbutyl, α-naphthylmethyl, β-naphthylmethyl, 1-(α-naphthyl)ethyl, 2-(β-naphthyl)ethyl, 4-(β-naphthyl)butyl, etc. Residues of 7-10 carbon atoms wherein phenyl is the aryl group are preferred.

Suitable $R_1$ and $R_2$ aryl groups are of 6-14 C-atoms and include phenyl, α- and β-naphthyl, phenanthryl, etc., preferably phenyl.

Suitable heterocyclic groups for $R_1$ and $R_2$ include mono- or bicyclic heterocycles with 1-3 N, O, or S hetero atoms, such as pyrryl, 2- or 3-thienyl, 2-, 3-, or 4-pyridyl, imidazolyl, pyrazolyl, triazolyl, oxazolyl, 2-thiazolyl, thiadiazolyl, oxadiazolyl, pyrimidyl, pyrazinyl, pyridazinyl, azepinyl, 1-, 3-, or 4-isoquinolyl, 2-, 3-, or 4-quinolyl, etc. Typically, such hetero groups have 5-10 ring atoms total and are aromatic.

The aromatic or heteroaromatic groups can be substituted by 1-3 halogen atoms (e.g. F, Cl, Br), up to three $C_1$-$C_4$-alkyl groups (preferably methyl), a nitro group, as well as up to three $C_1$-$C_4$-alkoxy groups (preferably methoxy), a $C_1$-$C_4$-alkoxy-carbonyl group or a $CF_3$-group.

Substituents for the amino group $R_1$ include the same alkyl, cycloalkyl, aralkyl and aryl groups described above. Mono- and di-substituted amino are included. Usually, only a single cycloalkyl, aralkyl, or aryl group is attached to the amino group.

When $R_1$ and $R_2$ jointly form a ring, they preferably form an alkylene bridge, such as tetramethylene, pentamethylene, hexamethylene, heptamethylene etc., thereby forming a ring of 6-9 atoms.

The alkyl residues in the alkoxy moieties of $R_3$ include straight-chain and branched, saturated hydrocarbon residues of 1-10 carbon atoms as mentioned above for the alkyl residues $R_1$ and $R_2$. The same is true for suitable aralkyl residues in the aralkoxy moieties of $R_3$, i.e., they likewise correspond to the residues recited for $R_1$ and $R_2$. Suitable heteroaryl residues in the heteroarylamino group of $R_3$ include those heterocyclic residues mentioned above in connection with $R_1$ and $R_2$.

Suitable monalkyl- or dialkylamino residues $R_3$ include those with alkyl groups of 1-4 carbon atoms, such as, for example: dimethylamino, diethylamino, diisopropylamino, di-n-butylamino, di-sec-butylamino, methylamino, ethylamino, propylamino, isopropylamino, n-butylamino, sec-butylamino, etc. Unsubstituted or substituted aryl or heteroaryl groups in the arylamino and heteroarylamino groups include those already defined above as aryl or heteroaryl groups in connection with $R_1$ and $R_2$.

The nature of the acid HY is completely noncritical as long as it is reaction compatible. Suitable mineral acids include hydrochloric acid, hydrobromic acid, sulphuric acid, nitric acid, phosphoric acid and suitable organic acids include $C_{1-10}$-hydrocarbon carboxylic acids such as acetic acid, oxalic acid, citric acid, succinic acid, butyric acid, maleinic acid, glutaric acid, propionic acid, malonic acid, sebacinic acid and so on.

The alkyl and aralkyl groups of $R_4$ generally are of 1-4 and 7-10 C atoms, respectively.

The reaction of the amidines or guanidines or their salts of Formula II with the corresponding O-silylated or O-alkylated 4-halocrotonic acid esters or amides of Formula III is suitably conducted in an inert polar solvent, such as acetonitrile, dimethylformamide (DMF), dimethylacetamide, N-methyl-pyrrolidone, sulfolane; or without a solvent, but, for example, in the presence of excess silylating reagent such as hexamethyldisilazane (HMDS) or trimethylchlorosilane (TCS), generally at 50°-200° C., and preferably at the boiling point of the reaction mixture, i.e., under reflux; or without any solvent. Typical reaction times are 0.5-100 hours. The amount of compound of Formula III relative to that of Formula II generally is 1-10; usually 1-6. Usually, stoichiometric amounts are used.

A further advantage of the process of this invention is that, starting with the 4-haloacetacetic acid ester or amide, in a single step, the reaction leads to the desired imidazole-4(5)-acetic acid esters or amides. The 4-halo-3-silyloxy- (preferably trimethylsilyloxy-) crotonic acid esters or amides of Formula III are, for this purpose, preferably prepared in situ from the corresponding 4-haloacetoacetic acid esters or amides by reacting with the appropriate silylating agent, preferably with hexamethyldisilazane (HMDS) or with the combination of HMDS with trimethylchlorosilane (TCS). This reaction per se, is carried out under conventional conditions for silylation, e.g., under reflux for 0.5-18 hours, using stoichiometric amounts; see also, e.g., S. H. Langer et al, J.O.C. 23: 50 (1958), whose disclosures are incorporated by reference herein. This simplifies the imidazole synthesis into a one-stage synthesis.

In the silylation portion of the reaction, it is frequently also advantageous to add, in addition to the base hexamethyldisilazane (HMDS), also a tertiary base, such as triethylamine, tripropylamine, tributylamine, diisopropylethylamine, or diazabicyclononene (DBN) or diazabicycloundecene (DBU). In order to accelerate the reaction and/or to increase the reaction temperature, it is frequently advantageous during the reaction to remove the hexamethyldisiloxane [$(CH_3)_3Si$-$O$-$Si(CH_3)_3$, bp 99°], which is produced during the condensation reaction, from the reaction mixture by distillation using a short distillation column.

All of the reactants of Formulae II and III can be successfully reacted as described above, and prepared as described below, irrespective of the precise nature (e.g., size, bulk, complexity, etc.) of the particular structures involved and their attendant effects on the underlying reactions, steric, electronic or otherwise.

All of the 4-halogenated 3-alkoxycrotonic acid esters or amides of Formula III can be fully conventionally produced, e.g., according to descriptions in the literature either by O-alkylation of 4-haloacetoacetic acid esters or amides, e.g. with esters of orthoformic acid [cf., e.g., U. Schmidt et al, "Monatshefte der Chemie" [Chemical Monthly] 102: 214 (1971), whose disclosures are incorporated by reference herein] or by halogenation of the corresponding 3-alkoxycrotonic acid esters or amides, for example with NBS [=N-bromosuccinimide] in $CCl_4$ [cf., e.g., D. G. F. R. Kostermans, Rec. 70: 79 (1951); E. G. Reid and W. R. Ruby, JACS 73: 1054 (1951), whose disclosures are incorporated by reference herein]. Silylations can be effected as described above. The typical reaction conditions for alkylation or aralkylation, e.g. reflux, temperatures, reaction times are analog to the described methods [U. Schmidt et al, "Monatshefte der Chemie" [Chemical Monthly] 102: 214 (1971); D. G. F. R. Kostermans, Rec. 70: 79 (1951); E. G. Reid and W. R. Ruby, JACS 73: 1054 (1951)]. The starting materials (e.g. 4-haloacetoacetic acid esters) are of commercial origin.

All of the starting amidines or guanidines and/or the salts thereof of Formula II can be fully conventionally prepared, e.g., according to the methods indicated in the literature, e.g. Houben/Weyl 11/2: 38-69 (1958); "The Chemistry of Amidines and Imidates", in "The Chemistry of Functional Groups" Editor Saul Patai, John Wiley and Sons (1975), whose disclosures are incorporated by reference herein, but preferably by conversion of correspondingly substituted nitriles into the associated imido ester hydrochlorides (cf., e.g., in this connection A. Pinner, "Die Imidoäther und ihre Derivate" [The Imido Ethers and Their Derivatives] (Berlin 1892), p. 53, whose disclosures are incorporated by reference herein) and subsequent reaction with the amines required for the synthesis of the desired products [e.g., analogously to F. L. Pyman, J. Chem. Soc. 1923: 3359; A. Pinner, loc. cit. p. 152, whose disclosures are incorporated by reference herein].

All of the imidazoleacetic acid derivatives of Formula I, are highly useful, e.g., as intermediates for valuable medicinal agents (e.g., antiinflammatory drugs) See, e.g., 5-imidazoleacetic acid derivatives described in JP No. 50084567 which posess antipyretic activity.

In addition, the compounds of Formula I can be used to prepare other compounds of Formula I, which in turn are useful as described herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following examples, all temperatures are set forth uncorrected in degrees Celsius; unless otherwise indicated, all parts and percentages are by weight.

EXAMPLE 1

4(5)-Ethoxycarbonylmethylimidazole

A solution of 8.25 g of the ethyl ester of 4-chloroacetoacetic acid in 250 ml of acetonitrile was combined with 19 ml of trimethylchlorosilane and 42 ml of hexamethyldisilazane. The reaction mixture was heated under reflux for one hour and then combined gradually in incremental portions with, in total, 31.2 g of formamidine acetate during a period of about 14 hours. The mixture was then allowed to cool, a mixture of 1 liter of ether/0.5 liter of hexane was added thereto, and the mixture was extracted five times with respectively 50 ml of water. The aqueous phase was washed once with an ether/hexane (1/1) mixture, filtered, and concentrated to dryness under vacuum. The residue was purified by column chromatography on silica gel with hexane/25-100% ethyl acetate and ethyl acetate/0-20% ethanol as the eluent, thus obtaining 6.6 g (85%) of the desired imidazoleacetic acid ester.

NMR (DMSO) 1.20 (t); 3.55; 4.05 (q); 6.85 (s); 7.45 (s)
IR (Film) 1735 cm$^{-1}$

EXAMPLE 2

4(5)-Ethoxycarbonylmethylimidazole

By replacing the 4-chloroacetoacetic acid ethyl ester of Example 1 by 3-ethoxy-4-chlorocrotonic acid ethyl ester (R. Findings, G. Zimmermann, U. Schmidt, Mh.Chem. 102: 214 [1971]; yield: 20%), 0.89 g (11%) of 4(5)-ethoxycarbonylmethylimidazole was obtained.

EXAMPLE 3

1,2-Diphenyl-4-ethoxycarbonylmethylimidazole

A mixture of 9.8 g of N-phenylbenzamidine [prepared according to Org. Synth. Coll. IV: 769 (1963)], 8.25 g of the ethyl ester of 4-chloroacetoacetic acid, 100 ml of hexamethyldisilazane, and 7 ml of triethylamine was heated overnight under reflux. The mixture was then diluted with 400 ml of ethyl acetate and washed five times with saturated sodium bicarbonate solution as well as water. After extraction of the aqueous phases with methylene chloride, the combined organic phases were dried and concentrated under vacuum. The residue was purified by column chromatography on silica gel with methylene chloride/0.2-1% isopropanol as well as toluene/40% ethyl acetate as the eluent. Yield: 9.1 g (59%) of the title compound.

NMR (CHCl$_3$) 1.28 (t); 3.75 (d); 4.2 (q); 7.1-7.4
IR (Film) 1735 cm$^{-1}$

EXAMPLE 4

2-(4-Bromo)phenyl-4-ethoxycarbonylmethylimidazole

A mixture of 5.88 g of 4-bromobenzamidine hydrochloride [prepared according to C. H. Andrewes, H. King, and J. Walker, Proc. Roy. Soc. [B] [London] 133: 20 (1946)] 4.12 g of the ethyl ester of 4-chloroacetoacetic acid, 10.5 ml of hexamethyldisilazane, and 3.5 ml of triethylamine was heated overnight under reflux. Subsequently the mixture was diluted with 500 ml of ethyl acetate and washed three times with respectively 100 ml of saturated sodium bicarbonate solution as well as three times with respectively 100 ml of water. After extraction of the aqueous phases with methylene chloride, the combined organic phases were dried over sodium sulfate and concentrated to dryness under vacuum. The residue was purified by column chromatography on silica gel with methylene chloride/0.1-6% isopropanol as the eluent, thus obtaining 3.8 g (49.9%) of the title compound, mp 165°-166° C. (toluene/ethyl acetate).

EXAMPLE 5

1-Methyl-2-phenyl-4-ethoxycarbonylmethylimidazole

A mixture of 6.12 g of N-methylbenzamidine hydrochloride, 4.95 g of the ethyl ester of 4-chloroacetoacetic acid, 18.5 ml of hexamethyldisilazane, 1.27 ml of trimethylchlorosilane, and 350 ml of acetonitrile was heated under reflux until the analytical TLC control no longer indicated any starting compound (about 72 hours). Then the mixture was allowed to cool, the volume of the reaction solution was reduced, by concentration under vacuum, to about one-half, thereafter combined with 200 ml of water, and repeatedly extracted with an ether/hexane (1/1) mixture. The combined organic phases were dried over magnesium sulfate, the solvent was removed under vacuum, and the residue was purified by column chromatography on silica gel with pentane/0-100% ethyl acetate as the eluent. Yield: 3.53 g (48%) of the title compound.

IR (Film) 1735 cm$^{-1}$
NMR (DMSO) 1.20 (t); 3.55; 3.72; 4.10 (q); 7.10; 7.3-7.7

The 1,5-position isomer was isolated in small amounts as a polar by-product, namely: 1-methyl-2-phenyl-5-ethoxycarbonylmethylimidazole.

EXAMPLE 6

1-Methyl-2-(3-chloro)phenyl-4-ethoxycarbonylmethylimidazole 10.25 g of N-methyl-3-chlorobenzamidine hydrochloride was first heated under reflux for 9 hours with 8.25 g of the ethyl ester of 4-chloroacetoacetic acid, 21 ml of hexamethyldisilazane, 6.4 ml of trimethylchlorosilane, and 250 ml of acetonitrile; then, in order to shorten the reaction time, the solvent was distilled off at a bath temperature of 110° C. The reaction solution was combined with 50 ml of hexamethyldisilazane and maintained at a bath temperature of 140° C. for one hour, whereafter it was cooled, combined with water, and extracted repeatedly with an ether/hexane (1/1) mixture. The combined organic phases were dried over magnesium sulfate, concentrated under vacuum, and the residue was purified by column chromatography on silica gel with hexane/10-100% ethyl acetate and/or methylene chloride/10% isopropanol as the eluent, thus obtaining 4.6 g (33%) of the title compound.

IR (Film) 1735 cm$^{-1}$
NMR (CHCl$_3$) 1.30 (t); 3.70; 3.73; 4.20 (q); 6.95; 7.3-7.7

The starting compound was prepared as follows:

(6a) 3-Chlorobenzimidoethyl Ester Hydrochloride

A solution of 50 g of 3-chlorobenzonitrile in ethanol and ether was saturated with anhydrous hydrogen chloride and subsequently allowed to stand at 3° C., thus crystallizing 70 g of 3-chlorobenzimidoethyl ester hydrochloride from the reaction solution.

(6b) N-Methyl-3-chlorobenzamidine Hydrochloride

A sodium ethylate solution prepared from 4.9 g of sodium in 86 ml of absolute ethanol was combined with 14.2 g of methylammonium chloride. After one hour of agitation, this suspension was added to 35 g of 3-chlorobenzimidoethyl ester hydrochloride and stored overnight at 3° C. After filtration, the solution was concentrated to dryness, and the residue was dissolved in water. The desired compound was obtained by precipitation with acetone/ether, thus isolating 24.8 g, mp 209° C.

EXAMPLE 7

4(5)-Methoxycarbonylmethyl-2-phenylimidazole

A mixture of 10 g of benzamidine hydrochloride, 7.55 g of the methyl ester of 4-chloroacetoacetic acid, 33 ml of hexamethyldisilazane, 6.3 ml of trimethylchlorosilane, and 300 ml of acetonitrile was refluxed for several hours until the analytical TLC control no longer showed any starting compound. Thereafter the reaction mixture was poured on 500 ml of water and extracted five times with respectively 100 ml of methylene chloride. The content of the organic phase was purified by column chromatography on silica gel with hexane/5-0-100% ethyl acetate as the eluent. After recrystallization from benzene, 6.5 g of the desired imidazole was obtained, mp 122°-124° C.

IR (Film) 1730 cm$^{-1}$

NMR (DMSO) 3.65; 7.05; 7.3-7.9

EXAMPLE 8

2-(2-Pyridyl)imidazole-4(5)-acetic Acid Methyl Ester

Under agitation, 4.73 g (0.03 mol) of 2-pyridylamidine hydrochloride [F. C. Schaefer and G. A. Peters, J. Org. Chem. 26: 412 (1961)] was heated to 140° C. for 14 hours with 4.5 g (3.6 ml=0.03 mol) of the methyl ester of 4-chloroacetoacetic acid, 12.65 ml (0.06 mol) of hexamethyldisilazane, and 14.3 ml (0.06 mol) of tributylamine. After cooling, the reaction mixture was taken up in methylene chloride and saturated sodium bicarbonate solution, and the aqueous phase was re-extracted several times with methylene chloride. After drying with $Na_2SO_4$, the methylene chloride phase was evaporated, thus obtaining 4.7 g (72%) of crude 2-pyridylimidazole-4(5)-acetic acid methyl ester which was homogeneous in the thin-layer system of ethyl acetate-methanol-triethylamine (75:20:5) ($R_f$=0.55). One-time filtration in ethyl acetate over 100 g of silica gel yielded 4.3 g (66%) of pure compound.

NMR (DMSO-D$_6$): 3.65 (s); 7.05 (s); 7.3 (m); 7.9 (m); 8.55 (m).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an imidazoleacetic acid derivative of the formula

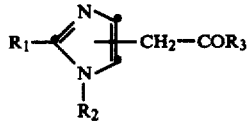

wherein $R_1$ is hydrogen; $C_{1-24}$-alkyl; $C_{5-7}$-cycloalkyl; $C_{7-14}$-aralkyl; $C_{6-14}$-aryl; a $C_{6-10}$-aromatic, mono- or bicyclic heterocycle of 5-10 total ring atoms, 1-3 being O, N or S atoms, the remainder being C-atoms; substituted $C_{6-14}$-aryl or said aromatic heterocycle each substituted by 1-3 halogen atoms, up to three $C_{1-4}$-alkyl groups, a nitro group, up to three $C_{1-4}$-alkoxy groups, a $C_{1-4}$-alkoxycarbonyl group or $CF_3$; amino; or amino substituted by $C_{1-24}$-alkyl, $C_{5-7}$ cycloalkyl, $C_{7-14}$-aralkyl or $C_{6-14}$ aryl;

$R_2$, independently, is hydrogen, alkyl, cycloalkyl, aralkyl, aryl, or a heterocyclic group, all as defined above for $R_1$; or $R_1$ and $R_2$ together are $C_{4-7}$ alkylene forming a ring with their connecting C-N bond; and $R_3$ is $C_{1-10}$-alkoxy, $C_{7-14}$-aralkoxy, amino, mono or di-$C_{1-4}$-alkylamino, pyrrolidino, piperidino, morpholino, arylamino, heteroarylamino, or substituted arylamino or substituted heteroarylamino, each of which is substituted in the aryl portion as recited above for $R_1$;

comprising reacting a corresponding amidine or guanidine of the formula

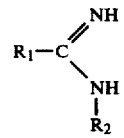

or a reaction compatible acid addition salt thereof wherein $R_1$ and $R_2$ are as defined above with an acetoacetic acid derivative of the formula

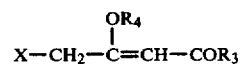

wherein $R_3$ is as defined above and

X is fluorine, chlorine, bromine, or iodine, and $R_4$ is tri-$C_{1-4}$-alkyl or tri-$C_{7-10}$-aralkylsilyl, $C_{1-4}$-alkyl, or $C_{7-10}$-aralkyl 2. A process of claim 1 comprising reacting a 4-haloacetoacetic acid derivative of the formula

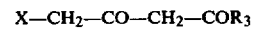

with a corresponding silylating, alkylating or aralkylating reagent to produce a compound of the formula

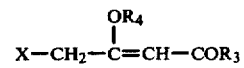

as described above and, in situ reacting the latter with a compound of the formula

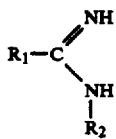
3. A process of claim 1 or 2 carried out under reflux conditions.
4. A process of claim 1 or 2 wherein the amidine or quanidine is reacted with the acetoacetic acid derivative in an inert polar solvent.
5. A process of claim 2 wherein the silylating reagent is hexamethyldisilazane alone or in combination with trimethylchlorosilane.
* * * * *